United States Patent [19]

Porter

[11] Patent Number: 4,459,278

[45] Date of Patent: Jul. 10, 1984

[54] COMPOSITION AND METHOD OF IMMOBILIZING EMETICS AND METHOD OF TREATING HUMAN BEINGS WITH EMETICS

[75] Inventor: Garry L. Porter, Wichita, Kans.

[73] Assignee: Clear Lake Development Group, Wichita, Kans.

[21] Appl. No.: 440,001

[22] Filed: Mar. 7, 1983

[51] Int. Cl.³ .................. A61K 33/44; A61K 31/74; A61K 47/00

[52] U.S. Cl. .................................. 424/10; 424/79; 424/125

[58] Field of Search ........................ 424/10, 79, 125

[56] References Cited

U.S. PATENT DOCUMENTS

| | | | |
|---|---|---|---|
| 1,542,006 | 6/1925 | Sauer | 424/125 |
| 1,589,081 | 6/1925 | Adler | 424/125 |
| 2,787,579 | 4/1957 | Van der Weel | 424/125 |
| 2,990,332 | 6/1961 | Keating | 424/79 |
| 3,091,574 | 5/1963 | Coletta et al. | 424/79 |
| 3,143,465 | 8/1964 | Keating | 424/79 |
| 3,499,960 | 3/1970 | Macek et al. | 424/79 |
| 3,934,007 | 1/1976 | Gussin et al. | 424/79 |
| 4,122,169 | 10/1978 | Geils | 424/125 |
| 4,140,652 | 2/1979 | Korshak et al. | 424/125 |
| 4,175,119 | 11/1979 | Porter | 424/10 |
| 4,221,778 | 9/1980 | Raghunathan | 424/79 |

FOREIGN PATENT DOCUMENTS 1218102  1/1971  United Kingdom .................. 424/79

Primary Examiner—Shep K. Rose

Attorney, Agent, or Firm—John H. Widdowson

[57] ABSTRACT

A therapeutic composition is coated with a mixture of an emetic chemical and an inert material. A method for reducing absorption into the body of a being of an emetic chemical while still retaining localized emetic activity comprises combining prior to ingestion of the chemical, the emetic chemical with a material that is substantially inert to a gastrointestinal environment such that when the combination is ingested and passed along the gastrointestinal tract, localized emetic activity is available while an undesirable amount of the emetic chemical is not absorbed into the body. A method of inducing emesis in the body of a being to preclude death from accidental or intentional overdosage of a therapeutic composition, which is normally of the type which if ingested by prescription is safe, but if excessively ingested is lethal while simultaneously reducing absorption of an emetic chemical into the body. The method comprising the steps of: combining an emetic chemical with a material that is substantially inert to a gastrointestinal environment; coating the surface of said therapeutic composition with the combination; controlling the quantity of said emetic chemical coated on the surface of the therapeutic composition such that no emesis ensues if normal prescription directions are followed or if no overdosage occurs; ingesting excessive quantities by the being of said therapeutic composition; and emesising by the being of the ingested excessive quantities of coated therapeutic composition in order to render the therapeutic compositions harmless and preclude death or serious illness to the being.

7 Claims, No Drawings

COMPOSITION AND METHOD OF IMMOBILIZING EMETICS AND METHOD OF TREATING HUMAN BEINGS WITH EMETICS

BACKGROUND OF THE INVENTION

1. Field of the Invention

This invention is related to a medical composition and the immobilization of emetics. More specifically, this invention provides for a therapeutic composition being coated with a mixture of an inert material and an emetic chemical.

2. Description of the Prior Art

My U.S. Pat. No. 4,175,119, issued Nov. 20, 1979, teaches a composition and method to prevent accidental and intentional overdosage with psychoactive drugs through coating of the drugs with an emetic chemical or an emesis-producing substance. A drawback to this invention has had to do with the toxicity of the emesis-producing substance in terms of neurological, cardio-toxic and hepatotoxic problems in the accumulation of these substances in the human while taking the psychoactive drugs according to prescription. What is needed and what has been invented by me is a means of immobilizing such emesis-producing substances as emetine and cephaeline in such a way that the emesis-producing substances would retain its emetic properties in the gastric lumen while simultaneously not being absorbed in the gastrointestinal tract but is allowed to pass therethrough without any major absorption.

SUMMARY OF THE INVENTION

It is therefore an object of this invention to provide a composition and a method which prevents accidental and intentional overdosage with any therapeutic composition while simultaneously preventing side effect problems caused by the absorption of "free" (unbound) emetine alkaloid into the body.

Still other objects will be apparent to those skilled in the art from the following description of this invention.

The foregoing objects are achieved according to the practice of this invention. Broadly, this invention comprises a therapeutic composition adapted to prevent drug overdosage and adapted for oral administration in addition to therapeutic ingredients having psychoactive characteristics including a coating of a mixture of an emetic chemical and an inert material on the surface of the therapeutic composition. The emetic chemical and the inert material have a ratio of emetic chemical to inert material of from about 2:1 to about 1:50. The coating includes between about 0.25 to 2.0 mg. of the emetic chemical comprising a major proportion of methyl cephaeline and cephaeline, and a minor proportion of psychotrine, O-methylpsychotrine and emetamine. The invention also broadly includes a method for reducing absorption into the body of a being of an emetic chemical while still retaining localized emetic activity by combining, prior to ingestion of the chemical, the emetic chemical with a material that is substantially inert to a gastrointestinal environment such that when the combination is ingested and passed along the gastrointestinal tract, localized emetic activity is available while an undesirable amount of the emetic chemical is not absorbed into the body. The invention also broadly comprises a method of inducing emesis in the body of a being to preclude death from accidental or intentional overdosage of a therapeutic composition, which is normally of the type which if ingested by prescription is safe, but if excessively ingested is lethal while simultaneously reducing absorption of an emetic chemical into the body. The method comprises the steps of: combining the emetic chemical with a material that is substantially inert to a gastrointestinal environment; coating the surface of said therapeutic composition with the combination such that the coating contains between about 0.25 and 2.0 mg. of the emetic chemical; controlling the quantity of the emetic chemical coated on the surface of the therapeutic composition such that no emesis ensues if normal prescription directions are followed or if no overdosage occurs; ingesting excessive quantities (at least 21 mg.) by the being of said therapeutic composition; and emesising by the being of the ingested excessive quantities of coated therapeutic composition in order to render the therapeutic compositions harmless and preclude death or serious illness to the being.

DETAILED DESCRIPTION OF THE INVENTION

This invention includes coating the surface of a therapeutic composition with a mixture of an inert material, and an emetic chemical selected from the group consisting of methyl ($C_{28}H_{38}O_4H_2$), cephaeline ($C_{28}H_{38}O_4H_2$), cephaeline emetine hydrochloride ($C_{30}H_{44}O_4N_2$2HCR), psychotrine ($C_{28}H_{36}O_4N_2$), O-methylpsychotrine, emetamine, ipecamine, hydro-ipecamine, ipecacunhic acid, and mixtures thereof. Preferably, the emetic chemical has a major proportion of methyl cephaeline and cephaeline, and a minor proportion of psychotrine, O-methylpsychotrine and emetamine. In a preferred embodiment of the invention, the emetic chemical comprises between about 40% wt. and 85% wt. of methyl cephaeline, between about 10% wt. and 40% wt. of cephaeline, between about 2% wt. and 12% wt. of psychotrine, between about 1% wt. and 6% wt. of O-methylpsychotrine, and between about 1% wt. and 6% wt. of emetamine. Additional embodiments of the invention provide for the emetic chemical additionally having between about 1% wt. and 6% wt. of ipecamine between about 1% wt. and 6% wt. of hydro-ipecamine, between about 1% wt. and 6% wt. of ipecacuanhic acid, and between about 1% wt. and 6% wt. of emetine hydrochloride.

The inert material may be any suitable inert material that is substantially inert to a gastrointestinal environment such that when the combination of the emetic chemical and inert material is ingested and passed along the gastrointestinal tract, localized emetic activity is available while an undesirable amount of the emetic chemical is not absorbed into the body. In a preferred embodiment of the invention, the inert material is selected from the group consisting of cation-exchange resin, activated charcoal, and mixtures thereof. Preferably, the ratio of the emetic chemical to the inert material ranges from between about 2:1 to about 1:50. The particle size of the cation-exchange resin may preferably vary from about 100 mesh to about 500 mesh (U.S. Sieve Series), and the particle size of the activated charcoal may likewise vary from about 100 mesh to about 800 mesh (U.S. Sieve Series).

I have discovered that a cation-exchange resin Dowex 50 (a trademark of Dow Chemical Co.), which is a sulfonated polystyrene cation-exchange bead resin with a 4% cross linkage and a 37 micrometer (200 to 400 mesh) diameter, interacts with an emetine hydrochloride irreversibly. The emetine-cation polystyrene complex is stable in vitro in simulated gastrointestinal environments and also in adverse reaction conditions, such as high salt, extreme acidic or basic pH conditions with no dissociation of the emetine compound from the resin. The structural components of benzolsoquinoline alkaloid emetines which are responsible for its biological activity has been shown to involve the distance between two aromatic rings, the angle between the nitrogen atoms, and the rings of planarity of the structure. The emetine-resin complex mixture exhibits emetic activity because the ionic interaction between the emetine and the cation-exchange resin are not involved in absorption and the resin-bound emetine fails to pass across a cell membrane.

The coating mixture of the inert material and the emetic chemical preferably has between about 0.26 mg. and 20 mg. of the emetic chemical. More preferably, the coating mixture includes between about 0.25 and 2.0 mg. of the emetic chemical. The quantity of the emetic chemical in the coating mixture and on the surface of the therapeutic composition should be controlled such that the dosage per coating per therapeutic composition would be so small as to be unnoticeable by itself, but such as to have an accumulation of a total dosage of at least 21 mg. of the emetic chemical if taken in any significant number would produce vomiting in 90% to 95% of the adult population in 10 to 15 minutes. The concentration per coating would be flexible to account for differing $MLD_{50}$ and therapeutically effective levels of dosage prescription. It has been discovered that the emetic chemical in the coating mixture should be controlled such as not to exceed 2.0 mg. per therapeutic composition. It has also been discovered that the coating mixture with the emetic chemical of this invention, depending on the constituents and concentration of constituents, is sensitive to lighting and should therefore be enveloped with an opaque coating means, well known to those skilled in the art.

It is important in this invention that the therapeutic composition be enveloped or coated with the mixture of inert material and emetic chemical instead of commingling or admixing the same with the therapeutic composition. The therapeutic significance is that the problematical toxic effects of the emetic chemical alkaloid can be obviated. The free emetic chemical is not allowed to enter the internal melieu of the body while at the same time the desired biological activity (inducement of emesis and anti-amoebic activity) of the emetic chemical is preserved because if a being accumulates sufficient therapeutic tablets or capsules in the stomach, the first active ingredient to be dissolved or touch the gastric lining would be the contents of the protective envelope of coating mixture of inert material and emetic chemical. Emesis would occur before any significant amount of therapeutic composition from the tablet or capsule could be absorbed. The mechanism of emesis production is primarily local in the stomach. Many of the psychoactive drugs inhibit emesis, an added reason for having the mixture of the inert material and the emetic chemical in a surface or first contact position. Coating, well known to those skilled in the art (e.g. pan coating air-suspension coating, compression coating, etc.), controls the rate and site of the release of the mixture of inert material and emetic chemical. The emetic chemical of this invention has been found to be much more effective than other emetics such as apomorphine, ammonium carbonate, cupric sulfate, tartar emetic, zinc sulfate, blacks mustard, sanguinaria, copper sulfate, eucalyptole, eucalyptus oil, glycynhiza, guaiacol, lobelia, potassium iodide, senega terebene, terpin hydrate, thyme, etc.

The therapeutic composition may come in any size tablet, causule, etc., such as 0.1, 0.5, 1, 5, 10, 25, 30, 50, 75, 100, 150, 200, 300, etc., mg. The therapeutic compositions may be neuroleptic drugs, e.g., there are eight classes: Phenothiazine (chlorpromazine, thioridiazine, trifluoperazine, fluphenazine, promazine, triflupromazine, mesoridazine, piperacetazine, acetophenazine, butaperazine, carphenazine, perphenazine, prochlorperazine, thiopropazine, thioproperazine, etc.), butyrophenones (haloperidol, triperidal, etc.), rauwalfia derivatives (Reserpine (rauwolfia), rauwolfia serpintina, etc.), benzoquinolizines (tetrabinazine, etc.), phenylpiperazine (oxypertine, etc.), acridan, indolic derivatives (molindone, etc.), and loxapine. The therapeutic composition may also be any of the anxiolytics/minor tranquilizers such as benzodiazepines (diazepam oxazepam, chlordiazepoxide, Librax (chlordiazepoxide and clidimium) etc.), diphenylmethanes, hydroxyzine (Atarax (hydroxyzine), Vistarial (hydroxyzine pamoate), etc.), chlormezanone, meprobamate; or sedative-hypnotics, such as barbiturates (secobarbital sodium, phenobarbital, amobarbital, pentobarbital, Carbital (pentobarbital and carbomel), mephobarbital, Tuinal (secobarbital and amobarbital), butabarbital, etc.), glutethimide, fluazepam, methprylon, ethchlorynol, promethazine, chloralhydrate, methaqualone, etc, or lithium carbonate, methylphenidate, Etrafon (perphenazine and amitriptylline), Triavil (perphenazine and amitriptylline); or anticonvulsants such as phenytoin sodium, mephenytoin, paramethadione, trimethadione, etc.; or an antiparkinsonian drug such as trihexyphenidyl, procyclidine HCI, benztropine, etc.; or antidepressants such as tricyclics (amitriptyline, imipramine HCI, nortriplyline HCI, desipramine HCI, etc.), doxepin, MAO inhibitors (tranylcypromine, isocarboxazid, nailamid, phenelzine, etc.) protrystyline HCI; or, anorexics such as amphetamines (amphetamine sulfate, dextro amphetamine, levo amphetamine, methamphetamine HIC), non-amphetamines (phentermine resin, diethylproprion, phenmetazine HCI, mazindol, etc.) etc; or analgesics such as narcotics (dolophin, meperedine, oxycodone, hydromorphone HCI, codiene, etc.), pentazocine HCI and derivative, acetylsalicylic acid, Fiorinal (butalbital, phenacetin, ASA, and caffiene), propoxyphene, propoxyphene napsylate, Coriciden (chlorpheniramine and ASA), acetaminophen, etc.; or muscle relaxants such asorphenadrine citrate, chlorzoxazone, carisoprodol, methocarbomal, phenylbutazine; or any of the antihistamines such as dimenhydrinate, pseudoephedrine, trimeprazine, gusarfenesin, Tus-Ornade (chlorpheniramine, phenylpropanolamine and caramiphen), Ornade (chlorpheniramine and phenylpropanolamine), promethazine HCI, phenylpropavolamine, pheniramine, pyrilamine, pyribenzamine, trimethobenzamide, diphenhydramine, chlorpheniramine, etc.; or any medicinal composition.

EXAMPLE I

Take any innocuous composition; coat the surface of the composition with a 1:1 ratio of a 300 mesh cation-exchange resin (e.g. Dowex 50) and 0.25 mg. of an emetic chemical having a major proportion of methyl cephaeline and cephaeline and a minor proportion of psychotrine, O-methylpsychotrine and emetamine; continuously, orally administer the coated therapeutic composition to a human being. Find that the human being will not vomit the coated composition after about 10 minutes when the accumulation of the emetic chemical is less than 21 mg., and also find less side effects problems caused by the absorption of "free" (unbound) emetic chemical alkaloid into the human being than if the same innocuous composition was coated with only the emetic chemical without the inert cation-exchange resin matter.

EXAMPLE II

Repeat Example I but allow the accumulation of the emetic chemical to be 21 mg. or more and find the human being disgorging the coated innocuous composition.

EXAMPLE III

Repeat Example I, but coat the surface of the therapeutic composition with a coating mixture having about 2.0 mg. of the emetic chemical and find similar results.

EXAMPLE IV

Repeat Example III with the emetic chemical of the emetic chemical-inert material mixture comprising about 40% wt. of methyl cephaeline, about 40% wt. of cephaeline, about 12% wt. of psychotrine, about 4% wt. O-methylpsychotrine, and about 4% wt. emetamine, and insuring that the emetic chemical on each innocuous composition does not exceed 2 mg. Find similar results.

EXAMPLE V

Repeat Example III with the emetic chemical of the emetic chemical-inert material mixture comprising about 60% wt. of methyl cephaeline, about 30% wt. of cephaeline, about 6% wt. of psychortine, about 2% wt. of O-methylpsychotrin, about 2% wt. of emetamine; and find similar results.

EXAMPLE VI

Repeat Example V with the emetic chemical of the emetic chemical-inert material mixture comprising about 56% wt. of methyl cephaeline, about 26% wt. of cephaeline, about 6% wt. of psychotrine, about 2% wt. of O-methylpsychotrine, about 2% wt. of emetamine, about 4% wt. ipecamine, about 4% wt. of hydro-ipecamine, and find similar results.

EXAMPLE VII

Repeat Example VI with the emetic chemical of the emetic chemical-inert material mixture comprising about 50% wt. of methylcephaeline, about 20% wt. of cephaeline, about 12% wt. of psychotrine, about 2% wt. of O-methylpsychotrine, about 2% wt. of emetamine, about 4% wt. of ipecamine, about 4% wt. of hydroipecamine, about 2% wt. of ipecacunhic acid, about 4% wt. of emetine hydrochloride, and find similar results.

Thus, by the practice of this invention there is a method of incorporating an emesis-producing substance (e.g. emetine alkaloid) into an inert insoluble support material. The methodology of the invention is to make available to the gastric lumen an emesis-producing substance whose biological activity within the lumen of the gastrointestinal tract is preserved and which will not be absorbed into the body, but passed in through the gastrointestinal tract and elminated from the body entirely.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A therapeutic composition adapted to prevent drug overdosage and adapted for oral administration in addition to therapeutic ingredients having psychoactive characteristics comprising a coating of a-mixture of an emetic chemical and an inert cation-exchange resin material on the surface of said therapeutic composition irreversibly interacting with an emetine alkaloid to form an emetine resin complex mixture which exhibits emetic activity because the ionic interaction between the emetine and the cation-exchange resin are not involved in absorption and the resin-bound emetine fails to pass across a cell membrane; said emetic chemical and said inert material having a ratio of emetic chemical to inert material of from about 2:1 to about 1:50; and said coating including between about 0.25 to 2.0 mg. of the emetic chemical comprising a major proportion of methyl cephaeline and cephaeline, and a minor proportion of psychotrine, O-methylpsychotrine and emetamine.

2. The therapeutic composition of claim 1 wherein the particle size of said cation-exchange resin varies from between about 100 mesh to about 500 mesh.

3. The therapeutic composition of claim 1 additionally including an opaque coating means surrounding said mixture of emetic chemical and inert material.

4. The therapeutic composition of claim 1 wherein said emetic chemical comprises between about 40% wt. and 85% wt. of methyl cephaeline, between about 10% wt. and 40% wt. of cephaeline, between about 2% wt. and 12% wt. of psychotrin, between about 1% wt. and 6% wt. of O-methylpsychotrine, and between about 1% wt. and 6% wt. of emetamine.

5. The therapeutic composition of claim 4 wherein said emetic chemical additionally includes between about 1% wt. and 6% wt. of ipecamine and between about 1% wt. and 6% wt. of hydro-ipecamine.

6. The therapeutic composition of claim 5 wherein said emetic chemical additionally includes between about 1% wt. and 6% wt. of ipecacuanhic acid.

7. The therapeutic composition of claim 6 wherein said emetic chemical additionally includes between about 1% wt. and 6% wt. of emetine hydrochloride.

* * * * *

UNITED STATES PATENT AND TRADEMARK OFFICE
Certificate

Patent No. 4,459,278                                Patented March 7, 1983

Gary L. Porter

Application having been made by Gary L. Porter, the inventor named in the patent above identified, and Clear Lake Development Group, the assignee, for the issuance of a certificate under the provisions of Title 35, Section 256, of the United States Code, adding the name of Ram P. Singhal as a joint inventor, and a showing and proof of facts satisfying the requirements of the said section having been submitted, it is this 16th day of Oct. 1984, certified that the name of the said Ram P. Singhal is hereby added to the said patent as a joint inventor with the said Gary L. Porter.

Fred W. Sherling,
*Associate Solicitor.*